(12) United States Patent
Tognetti et al.

(10) Patent No.: US 12,161,569 B2
(45) Date of Patent: Dec. 10, 2024

(54) PROSTHETIC HAND SYSTEM

(71) Applicant: FABRICA MACHINALE S.R.L., Navacchio (IT)

(72) Inventors: Alessandro Tognetti, Navacchio (IT); Gabriele Donati, Pescia (IT); Michele Bacchereti, Navacchio (IT); Luca Ferretti, Navacchio (IT); Giampaolo Pellicci, Navacchio (IT); Nadia Vitetta, Navacchio (IT); Nicola Carbonaro, Navacchio (IT)

(73) Assignee: FABRICA MACHINALE S.R.L., Navacchio (IT)

( * ) Notice: Subject to any disclaimer, the term of this patent is extended or adjusted under 35 U.S.C. 154(b) by 105 days.

(21) Appl. No.: 16/813,003

(22) Filed: Mar. 9, 2020

(65) Prior Publication Data

US 2020/0330246 A1 Oct. 22, 2020

Related U.S. Application Data

(63) Continuation of application No. 14/761,298, filed as application No. PCT/IB2014/058239 on Jan. 13, 2014, now Pat. No. 10,583,017.

(30) Foreign Application Priority Data

Jan. 16, 2013 (IT) .............................. PI2013A000004

(51) Int. Cl.
*A61F 2/58* (2006.01)
*A61F 2/70* (2006.01)
(Continued)

(52) U.S. Cl.
CPC .............. *A61F 2/583* (2013.01); *A61F 2/586* (2013.01); *A61F 2/72* (2013.01);
(Continued)

(58) Field of Classification Search
CPC ....................................................... A61F 2/583
See application file for complete search history.

(56) References Cited

U.S. PATENT DOCUMENTS

| 1,464,842 | A | * | 8/1923 | Burgan | ..................... A61F 2/78 |
| | | | | | 623/63 |
| 4,114,464 | A | * | 9/1978 | Schubert | .............. B25J 15/0213 |
| | | | | | 623/64 |

(Continued)

FOREIGN PATENT DOCUMENTS

| JP | H09-510128 A | 3/1995 |
| JP | 2000-325375 A | 11/2000 |

(Continued)

*Primary Examiner* — Jacqueline Woznicki
(74) *Attorney, Agent, or Firm* — STEPTOE LLP; Carl B. Wischhusen

(57) ABSTRACT

A prosthetic hand structure including at least one mechanical finger having a metacarpal support and a proximal stiff link connected to the metacarpal support by a proximal cylindrical joint. The mechanical finger includes a transmission member connected to the proximal stiff link. The transmission member includes a worm screw integral to the proximal stiff link. The transmission member includes a flexible rack having a first end portion, pivotally connected to the metacarpal support, and a second end portion arranged to engage with the threaded profile of the worm screw at an engagement zone of the flexible rack. The structure also includes an actuator mounted to the mechanical finger and to actuate the worm screw, causing it to rotate about its rotation axis, in such a way that, when the actuator moves the worm screw, the mechanical finger extends or flexes.

13 Claims, 11 Drawing Sheets

(51) Int. Cl.
*A61F 2/72* (2006.01)
*A61F 2/68* (2006.01)
*A61F 2/76* (2006.01)

(52) U.S. Cl.
CPC . *A61F 2002/587* (2013.01); *A61F 2002/6836* (2013.01); *A61F 2002/701* (2013.01); *A61F 2002/704* (2013.01); *A61F 2002/762* (2013.01); *A61F 2002/763* (2013.01); *A61F 2002/764* (2013.01)

(56) References Cited

U.S. PATENT DOCUMENTS

| | | | |
|---|---|---|---|
| 4,256,331 | A | 3/1981 | Schwanz et al. |
| 4,345,282 | A * | 8/1982 | Miyakawa ......... G11B 15/6656 360/130.22 |
| 4,364,593 | A | 12/1982 | Maeda |
| 4,763,276 | A | 8/1988 | Perreirra et al. |
| 5,080,682 | A * | 1/1992 | Schectman ............. A61F 2/583 623/64 |
| 5,246,465 | A | 9/1993 | Rincoe et al. |
| 5,326,369 | A * | 7/1994 | Schectman ............. A61F 2/586 623/64 |
| 5,413,611 | A | 5/1995 | Haslam, II et al. |
| 5,888,246 | A * | 3/1999 | Gow ....................... A61F 2/583 623/64 |
| 6,344,062 | B1 * | 2/2002 | Abboudi ................. A61F 2/54 623/24 |
| 6,896,704 | B1 | 5/2005 | Higuchi et al. |
| 8,808,397 | B2 | 8/2014 | Gow |
| 8,864,845 | B2 | 10/2014 | van der Merwe et al. |
| 2001/0028174 | A1 | 10/2001 | Matsuda et al. |
| 2006/0094989 | A1 | 5/2006 | Scott et al. |
| 2008/0215162 | A1 * | 9/2008 | Farnsworth ............... A61F 2/68 600/587 |
| 2008/0288088 | A1 | 11/2008 | Langenfeld et al. |
| 2010/0036507 | A1 * | 2/2010 | Gow ....................... A61F 2/583 623/64 |
| 2010/0191343 | A1 | 7/2010 | Puchhammer et al. |
| 2010/0268351 | A1 * | 10/2010 | van der Merwe ..... G01C 21/16 600/595 |
| 2010/0274365 | A1 | 10/2010 | Evans et al. |
| 2011/0257765 | A1 | 10/2011 | Evans et al. |
| 2011/0270416 | A1 | 11/2011 | Lee et al. |
| 2012/0109337 | A1 * | 5/2012 | Schulz ..................... A61F 2/586 623/64 |
| 2012/0123558 | A1 | 5/2012 | Gill |
| 2013/0030550 | A1 | 1/2013 | Jopek et al. |
| 2013/0041476 | A1 | 2/2013 | Schulz |
| 2013/0226315 | A1 | 8/2013 | Varley |
| 2014/0257521 | A1 | 9/2014 | Flaven et al. |
| 2014/0288665 | A1 * | 9/2014 | Gill ....................... A61H 1/0288 623/24 |
| 2014/0324189 | A1 | 10/2014 | Gill et al. |
| 2015/0173918 | A1 | 6/2015 | Herr et al. |
| 2015/0230941 | A1 | 8/2015 | Jury |
| 2015/0265428 | A1 | 9/2015 | Akiba |
| 2015/0351935 | A1 | 12/2015 | Donati et al. |
| 2015/0374515 | A1 | 12/2015 | Meijer et al. |
| 2016/0051383 | A1 | 2/2016 | Goldfarb et al. |
| 2016/0074181 | A1 | 3/2016 | Segil et al. |
| 2017/0087719 | A1 * | 3/2017 | Tsuchiya ................. B25J 9/1651 |

FOREIGN PATENT DOCUMENTS

| | | | |
|---|---|---|---|
| JP | 2009-517155 A | 4/2009 | |
| WO | WO-9524875 A1 * | 9/1995 | ............ A61F 2/583 |
| WO | 2012/039479 A1 | 3/2012 | |

* cited by examiner

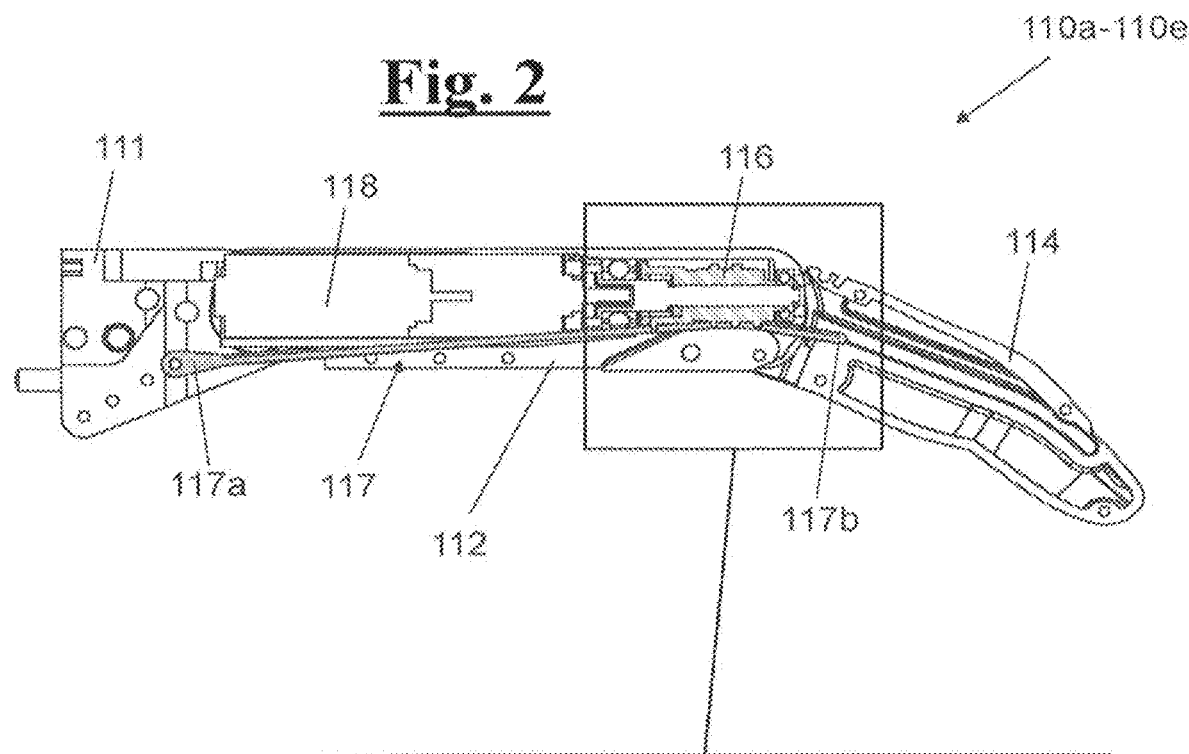
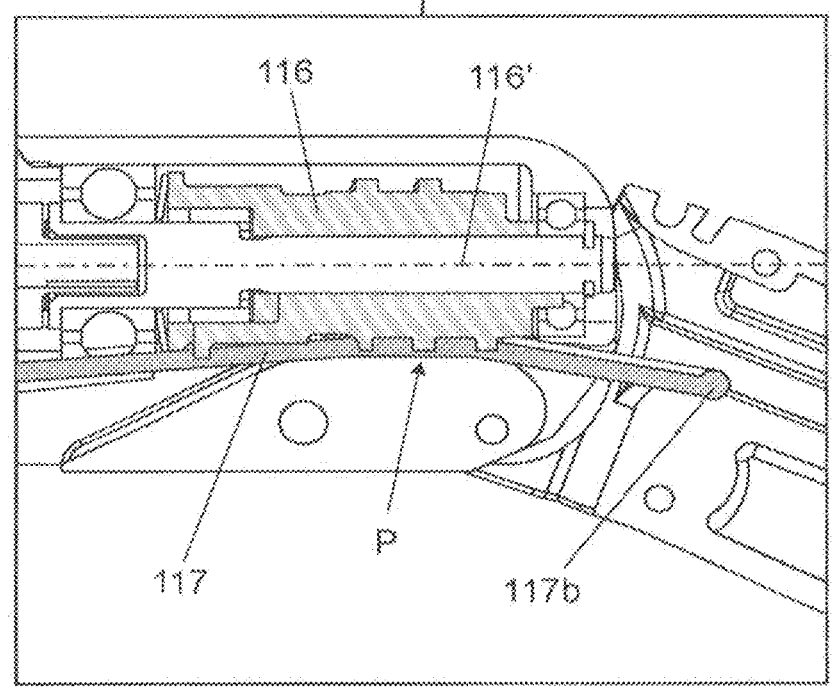

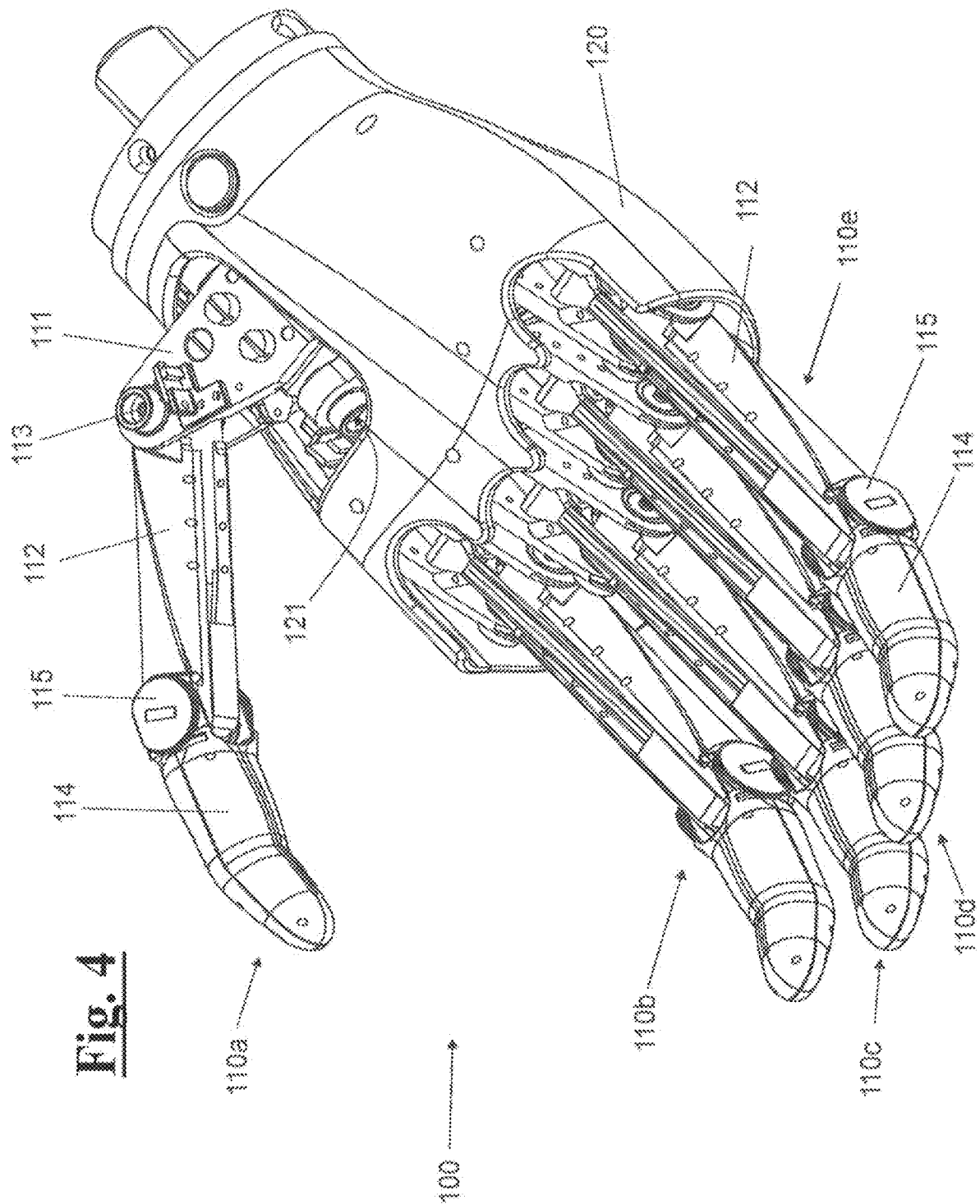

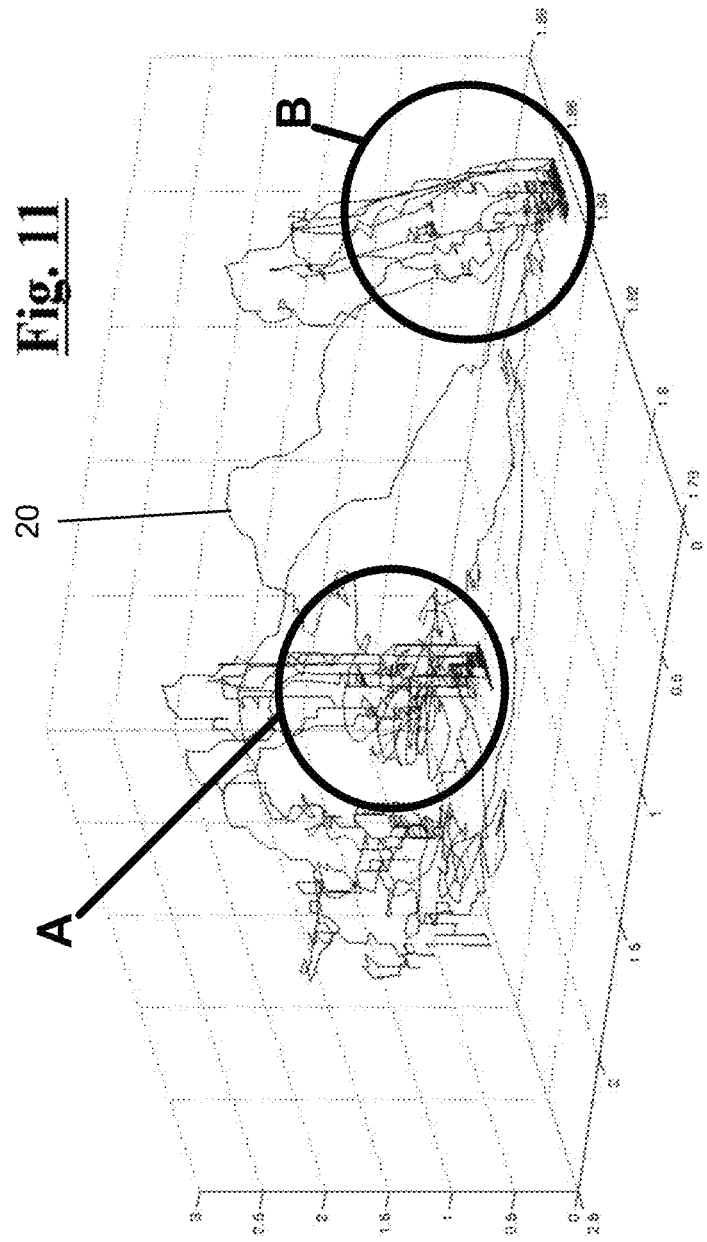

PROSTHETIC HAND SYSTEM

CROSS-REFERENCE TO RELATED APPLICATIONS

This application is a continuation of U.S. patent application Ser. No. 14/761,298, filed Jul. 15, 2015, and now U.S. Pat. No. 10,583,017. This application also claims priority to International Application No. PCT/IB2014/058239, filed Jan. 13, 2014, which claims priority to Italian Patent Application No. PI2013A000004, filed Jan. 16, 2013. These applications are incorporated by reference in their entirety.

FIELD

The present disclosure relates to the field of joint prostheses, which are used in case of partial or total amputations of the upper limbs.

More in detail, the disclosure relates to an actuating mechanical finger structure of a total or partial hand prosthesis, which is operated responsive to data obtained from sensors influenced by the intentions of a patient.

BACKGROUND

As well known, in the past years joint prostheses achieved relevant technological progresses, in particular concerning miniaturization of electronic and mechanical components, and improved software capable of simulating an anatomical behavior.

In particular, relevant known improvements relate to the mechanical transmission and the electronic computation adopted for actuating gripping ends, especially for hand prostheses, very common in prosthetic technology.

The replacement of a hand, or only of some phalanxes is common for the high occurrence of amputations of this area of the body, for example deriving from workplace injuries or other causes such as road accidents.

The above developments have been achieved by recent hand prostheses having both high biomimetic features and high gripping configuration with respect to those obtained by the former electromechanical prosthesis.

However, it is not easy to provide prosthesis of the hand or only of phalanxes capable of really meeting the needs of a patient. In fact, the motion of the fingers of a hand is extremely complex to reproduce, for the large number of anatomical parts, in particular joints, tendons and muscles present in a hand.

On the market various solutions exist of hand prosthesis, or of single phalanxes. Such solutions differ from one another especially for the type of operation of the fingers.

In US2008319553A1 and WO2010018358A2, for example, prostheses are described where the actuators are arranged in the palm of the hand of the prosthesis.

In particular, in US2008319553A1 a frame is provided to which at least one finger graft is articulated that rotates about an axis by an actuator and a transmission, arranged in the palm of the hand.

In WO2010018358A2, instead, an actuator for each finger of the prosthesis is presented. The fingers are, in this case, independent from each other, but they need in any case a complete hand structure for mounting the actuators.

The above solutions have the disadvantage that fingers cannot be replaced separately, since only the complete limb can be replaced.

Such drawbacks can be overcome, as suggested in US2010191343A1 and WO2007063266A1, where the actuators are located distally in the fingers same. However, they have further problems.

In particular, US2010191343A1 describes a prosthesis having a heavy and cumbersome actuation of the fingers. Owing to its large size, it is not possible to provide small hand prosthesis, that would be necessary for achieving an optimal biomimetic in case the patient is a woman or a child. Furthermore, the high weight can cause high loads to the stump of the patient, thus tiring the muscles, in particular at the interface between the stump and the prosthesis.

In WO2007063266A1, instead, an attempt is made to solve the problem of the encumbrance and of the weight, by simplifying the phalanx joints.

However, such solution is very stiff. In particular, an excessive stiffness of the phalanxes prevents the prosthesis from dampening compressing stresses applied, even incidentally, to the fingers. Such loads are therefore transferred integrally to the stump of the user, resulting tiring and painful.

There are also sensors for hand prosthesis, i.e. the parts that detect and transmit data relating to the will of the patient to carry out movements.

In this field, contrarily to prosthetic mechanical transmissions and electronic computerizations, in the last years only minor developments have been made.

The known techniques provide normally an acquisition of ElectroMyoGraphic signals, or myoelectric, by means of EMG sensors arranged in contact with the skin of the stump of the patient. This way, it is possible to measure the muscle activity of the stump of the patient by a measurement of the voltage at the skin level.

An example of this technique is given in WO0113778, in which at least one EMG sensor is used for detecting the muscle contractions of the patient and triggering the subsequent operation of the prosthesis.

However, to ensure a sufficient detection precision several EMG sensors are needed.

More in detail, usually a first EMG sensor is arranged at the agonist muscle and a second EMG sensor is arranged at the antagonist muscle.

This causes a high cost owing to the high cost of the EMG sensors.

Furthermore, by an EMG sensor the zone of skin where the electric signal is higher is detected, and this zone, as understandable, changes from patient to patient.

A system of sensors including only EMG sensors requires a customization of the prosthesis that increases further the costs of the product.

Other examples of prosthetic systems of the prior art with similar drawbacks are described also in WO2011/087382, EP1195151 and WO03/017876.

SUMMARY

Existing limitations associated with the foregoing, as well as other limitations, can be overcome by a prosthetic hand structure and method of operating mechanical fingers of the prosthetic hand structure. Briefly, and in general terms, the present disclosure is directed to various embodiments of a prosthetic hand structure. A prosthetic hand structure capable of measuring the intentions of a patient, through the acquisition of a plurality of data, and of operating the mechanical fingers of a total or partial hand prosthesis responsive to data computed is disclosed.

In one embodiment, a prosthetic structure for a hand provides a finger actuation of minimum encumbrance, in order to replace a hand of a patient or user. The hand to be replaced may any size, including small in size, like that of a woman or of a child, ensuring also high biomimetic features. Further, the prosthetic structure may be light enough to avoid tiring the stump of a user. It has also been contemplated that the prosthetic structure dampens the compressive stress on the fingers, to avoid painful effects on the stump.

In one embodiment, the prosthetic hand structure has a structure in which the finger actuators are located in the fingers, in such a way that each finger is independent, so that the structure can be implemented to replace not only a hand, but even separate fingers or phalanxes. Also, the fingers may be modular elements, interchangeable with each other, in order to maximize the use of each component, with subsequent savings. In other embodiments, the fingers may vary in size and shape. In one embodiment, the structure of the prosthetic hand is such that the finger actuation ensures a high speed of opening and closing the fingers to ensure high biomimetic characteristics.

The prosthetic hand structure may also allow a patient or user to operate the prosthesis in a way much easier than the presently existing solutions. The prosthetic structure for the hand may be for carrying out a plurality of possible movements of the mechanical fingers, each of them corresponding to a particular gripping pattern, or to a predetermined action.

Furthermore, the prosthetic hand structure may have a system of sensors capable of selecting a plurality of possible movements of the mechanical fingers. These movements may be as close as possible to those desired by the patient. In one embodiment, the prosthetic hand structure may have a system of sensors that makes the above selection on the basis of the spatial position, of the speed and of the accelerations of the arm, as well as on the basis of the relative location of some parts of the prosthesis. However, other criteria may be used to control the prosthesis.

The prosthetic hand structure may be mass-produced, such that it is not necessary to produce a customized prosthesis for each patient. This would result in noticeable savings in the production. Furthermore, force sensors can be used of the type with adjustable resistances; these sensors involve lower costs and feature a linear proportion between the force to which they are subjected and their conductance.

In one embodiment a prosthetic structure for a hand includes at least one mechanical finger, and typically five mechanical fingers including a mechanical thumb. The mechanical finger has a metacarpal support, a proximal stiff link connected to the metacarpal support by a proximal cylindrical joint. The proximal stiff link may be arranged for carrying out a rotation of predetermined amplitude $\varphi$ with respect to the metacarpal support about an axis of the proximal cylindrical joint. In this embodiment, the prosthetic structure includes a transmission member connected to the proximal stiff link that is arranged to actuate the proximal stiff link for causing the rotation of predetermined amplitude $\varphi$. The transmission member may include a worm screw integral to the proximal stiff link and having a threaded profile. The worm screw may be arranged for carrying out a rotation about its longitudinal axis. The transmission member also includes a rack. In one example, the rack is a flexible rack, having a first end portion, pivotally connected to the metacarpal support, and a second end portion which is adapted to engage with the threaded profile of the worm screw at an engagement zone of the rack.

Also, the prosthetic hand structure may include an actuator arranged to move the transmission member. The actuator may be mounted to the mechanical finger and adapted to actuate the worm screw. Actuating the worm screw causes it to rotate about the longitudinal axis, in such a way that, when the actuator moves the worm screw, a moving away/approaching movement of the engagement zone is caused away from/towards the first end portion. This causes the rotation of predetermined amplitude, in a direction of rotation, or in an opposite direction, of the proximal stiff link about the axis of the proximal cylindrical joint, the rotation of predetermined amplitude $\varphi$ corresponding to the extension/flexion movement of the mechanical finger. In this example, the moving away/approaching movement generates the extension/flexion movement of the mechanical finger. The use of a flexible rack allows the use of the same component, i.e. the rack, both as pulling element, in a flexion movement, and as pushing element, in an extension movement.

This example provides a system of actuation of the mechanical fingers that is light and has minimum lateral encumbrance, in order to provide also a hand prosthesis of small size. Furthermore, the prosthetic structure of this example, owing to the minimum weight, minimizes tiring of the stump, which can thus bear many load types.

The mechanical finger structure of the above examples provides the actuator mounted directly to the mechanical finger, which allows the change of separate fingers of the patient in case of partial amputation of the hand. Furthermore, the high flexibility of the rack allows buckling, such that compressive loads receive a high damping and are not transferred integrally to the stump, as it would occur in case of stiff mechanical fingers.

In one embodiment, a voltage source may be provided which can supply electric energy for operating the prosthetic structure, and, in particular the actuators and the sensors. Such source can be, for example, an accumulator or a rechargeable battery, or the like.

In this example of the prosthetic hand structure, the use of a screw/rack system allows for high energy efficiency. In this embodiment, the screw/rack system has a very low mechanical efficiency, for example lower than about 0.5. This ensures an irreversibility of the movement which keeps the prosthesis blocked, once reached the predetermined position, without making use of external energy. The screw/rack system requires therefore the use of this source of electric current only during the step of arranging the mechanical fingers in the working predetermined configuration.

In one embodiment, the rotation of predetermined amplitude $\varphi$ of the proximal stiff link with respect to the metacarpal support lays in a plane $\pi$ substantially orthogonal to the axis of the proximal cylindrical joint. The longitudinal axis about which the worm screw is adapted to carry out its own rotation lays in the plane $\pi$.

In one embodiment, each mechanical finger also includes a distal stiff link connected to the proximal stiff link by a distal cylindrical joint, which is adapted to carry out a rotation of predetermined amplitude with respect to the proximal stiff link about an axis of the distal cylindrical joint. The distal cylindrical joint may be under-actuated by a mechanical reduction carried out by a couple of gears or by a belt that is wound/unwound in guiding grooves. The under-actuation may allow a higher bio-mimetic of the prosthetic limb and assists to grip objects, for example cylinders of small diameter, with a precision otherwise not obtainable in an easy way.

In yet another embodiment, the distal cylindrical joint can provide a condition of stiff constraint, in such a way that the mechanical finger is substantially a mono-phalangeous finger. This may provide a reduction of costs of the product and an increase of performances versus force, since a certain amount of the energy for the system is not consumed by operating the distal part.

In one embodiment, the prosthetic hand structure includes a plurality of mechanical fingers and a metacarpal base connected to the metacarpal support of each mechanical finger. In this embodiment, the prosthetic structure can replace a whole hand, including the metacarpal portion of the hand same.

In one embodiment, if the mechanical finger is a mechanical finger for the thumb, then the metacarpal base is connected to the mechanical finger for the thumb by a rotational joint for enabling a rotation about its own longitudinal axis. This provides to the mechanical finger for the thumb an abduction/adduction degree of freedom. The rate of abduction/adduction may allow enlarging the range of possible gripping configurations that the prosthetic hand can carry out.

In one embodiment, a selection device which is adapted to select a predetermined working configuration among a plurality of possible predetermined working configurations is also provided. The selection device may be adapted to operate the actuator of the prosthesis to obtain the selected working configuration.

By way of example only, the prosthetic structure may include at least one feedback position sensor. In one embodiment the feedback position sensor is a Hall-effect sensor, associated with each mechanical finger. The feedback position sensor is adapted to measure the position of the proximal stiff link with respect to the metacarpal support, and then to determine in real time the amplitude ($\varphi$) of the rotation. The feedback position sensor may be configured to generate instantly a corresponding feedback signal and to transmit this feedback signal to a control unit. The control unit is configured to analyze the feedback signal and to operate the actuator for actuating the worm screw until the amplitude ($\varphi$) determined in real time reaches a predetermined amplitude ($\varphi$). In this example, it is possible to make an operation feedback loop control that allows a higher precision in handling the mechanical finger. Furthermore, the use of Hall-effect sensors allows avoiding contacts of mechanical type between the proximal stiff link and the metacarpal support.

In yet another embodiment, the prosthetic structure may include additional sensors. In one example, the structure includes at least one myoelectric sensor, or EMG sensor, which is arranged, in use, in contact with the stump of the patient. The myoelectric sensor may be configured to measure a voltage associated with activation of an agonist and/or antagonist muscle of the stump of the patient and may generate a relative myoelectric signal. The structure also may include a plurality of force sensors arranged, in use, in contact with the stump of the patient and distributed on a predetermined surface of the stump. The plurality of force sensors may be configured to measure a plurality of pressure data corresponding to a predetermined muscle configuration achieved by the patient and may generate at least one corresponding pressure distribution signal on the stump. These sensors may be used alone or in combination with one another.

In this example, the prosthesis hand structure may include a control unit configured to analyze the myoelectric signal and the signal of pressure to carry out a selection of a predetermined working configuration. For example, a gripping configuration, among a plurality of possible predetermined gripping configurations. The control unit may be configured to operate the actuator to obtain the selected working configuration. The selection obtained from the control unit may be carried out by comparing the myoelectric signal and the pressure distribution signal predetermined by the sensors with a plurality of signals associated with predetermined working configurations. This makes it possible for a patient to use, for handling the mechanical fingers, the same muscles that a person without amputations would use, so that the prosthetic integration is as natural as possible.

In one embodiment of the prosthetic hand structure, it is possible to install on the prosthesis a single EMG sensor, and to compensate for the lack of a second or of a third EMG sensor using force sensors. Given the significant cost differences between EMG sensors and force sensors, this embodiment of the prosthetic hand structure allows installation of many force sensors, forming a kind of matrix of sensors, which can be distributed on a wide area of the stump. There would be no need for a preliminary step to define a specific zone of application where the muscle signal is more intense, as instead it has to be done for EMG sensors. This provides substantially all-purpose prosthesis, or that in any case does not require adjusted according to the needs of each patient, which can be used for patients with morphological features also very different from each other. This embodiment is cheaper than prior prosthetics, because it has cheaper parts and a less expensive production, since it does not require customization work for the patient. In this embodiment, it is preferred that the EMG sensor is located near the elbow of the patient.

In one embodiment, the prosthetic structure may include an inertial sensor. In one example, the structure may include an inertial sensor configured to measure the spatial orientation of the prosthetic structure with respect to a predetermined direction. The inertial sensor may generate a corresponding spatial position signal, and transmit the spatial position signal to the control unit. In another example, the prosthesis may include an inertial sensor configured to measure at least one linear and/or angular speed and/or acceleration, of the prosthetic structure, to generate a corresponding kinematic signal, and to transmit the kinematic signal to the control unit. These inertial sensors may be used separately or in combination with one another. In this example, the control unit may be configured to carry out the selection of the possible working configurations also on the basis of the spatial position signal and/or the kinematic signal.

By adding a filter further in the search of the working configurations that the user wishes carry out, this may enlarge the field of configurations obtainable and/or speeding up the procedure of selection.

In one embodiment, the prosthetic structure may also include a first inertial sensor configured to measure at least one linear and/or angular speed and/or acceleration, of the prosthetic structure. The first inertial sensor may generate a corresponding kinematic signal, and transmit the kinematic signal to the control unit. A second inertial sensor may also be included. The second inertial sensor may be located on the forearm, if the first inertial sensor is located on the hand, or on the hand if the first inertial sensor is located on the forearm. The second inertial sensor arranged for measuring at least one linear and/or angular speed and/or acceleration, respectively, of the forearm or the hand. The second inertial sensor may generate a corresponding reference spatial position signal, and transmit the reference spatial position signal to the control unit. In this embodiment, the control unit may be configured to compare the spatial position signal with the reference position signal, obtaining a relative position value between hand and forearm. The control unit also may be configured for carrying out the selection of possible gripping configurations on the basis of the relative position value between hand and forearm.

The relative position between the arm and the hand allows determining the configuration of the wrist, which can give a further discrimination with respect to possible actions that the user wishes to carry out.

In one embodiment, the prosthetic structure may include at least one position sensor for the mechanical thumb, such as a Hall-effect sensor. This position sensor may be configured to measure the direction of the mechanical finger for the thumb with respect to the metacarpal base, to generate a corresponding thumb position signal, and to transmit the thumb position signal to the control unit. In this embodiment, the control unit may be configured to carry out the selection of possible gripping configurations also on the basis of the thumb position signal.

In this embodiment, the position sensor for the thumb can coincide, structurally, with the feedback position sensor used for mechanical operation in feedback loop, even if the object of the signal generated is radically different. The position of the thumb detected by the actual position sensor may be used for giving data concerning the angle of abduction/adduction of the thumb, which is essential in this selection. Such angle does not correspond with one actuated degree of freedom, and therefore it can be changed only externally, for example using the other hand. For this reason this angle is unknown to the control unit, and has to be detected by a suitable sensor.

The prosthesis structure, according to certain embodiment, can include a single type of sensor as above described, or any combination thereof.

According to another embodiment, a prosthetic hand structure includes at least one mechanical finger. The mechanical finger includes a metacarpal support, a proximal stiff link connected to the metacarpal support by a proximal cylindrical joint. The proximal stiff link may be arranged for carrying out a rotation of predetermined amplitude φ with respect to the metacarpal support about an axis of the proximal cylindrical joint. The prosthetic hand structure also may include an actuator arranged to cause the rotation of predetermined amplitude φ of the proximal stiff link with respect to the metacarpal support. A control unit may be included to operate the actuator to obtain the rotation of predetermined amplitude φ.

In this embodiment, the prosthetic structure provides at least one sensor. The sensor may be a myoelectric sensor in contact with the stump of the patient. The myoelectric sensor may be configured to measure a voltage associated with activation of an agonist and/or antagonist muscle of the stump of the patient and generate a relative myoelectric signal. In another example, the sensor may be one or a plurality of force sensors in contact with the stump of the patient and distributed on a predetermined surface of the stump. The plurality of force sensors may be configured to measure a plurality of pressure data corresponding to a predetermined muscle configuration achieved by the patient and generate at least one corresponding pressure distribution signal on the stump. In yet another example, the sensor may be an inertial sensor configured to measure the spatial orientation of the prosthetic structure with respect to a predetermined direction, generate a corresponding spatial position signal, and transmit the spatial position signal to the control unit. Still further, the sensor of this embodiment may be an inertial sensor configured to measure at least one linear and/or angular speed and/or acceleration, of the prosthetic structure, generate a corresponding kinematic signal, and transmit the kinematic signal to the control unit. A position sensor, such as a Hall-effect sensor, may be used. The position sensor may be configured to measure the direction of the mechanical finger for the thumb with respect to the metacarpal base, generate a corresponding thumb position signal, and transmit the thumb position signal to the control unit. In this embodiment, the control unit may be configured to carry out the selection of possible gripping configurations also on the basis of the thumb position signal. These various sensors may be used separately or in any combination with one another.

In this embodiment, the control unit may be configured to analyze the myoelectric signal, the pressure distribution signal, the spatial position signal, the kinematic signal, and/or the thumb position signal, to carry out a selection of a predetermined working configuration. In one example, the predetermined working configuration may be a gripping configuration, among a plurality of possible predetermined gripping configurations. Further, the control unit may operate the actuator to obtain the selected working configuration.

Other features and advantages will become apparent from the following detailed description, taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 shows a cross section of the mechanical finger of the exemplary embodiment of prosthetic structure of FIG. 1;

FIG. 2A shows an enlarged view of the portion of mechanical finger of FIG. 2 where it is shown in mesh between worm screw and rack;

FIG. 4 shows an exemplary embodiment of the hand prosthetic structure, where a plurality of mechanical fingers and a metacarpal base are provided;

FIG. 11 shows an example of a 3D vector space generated by the signals detected by the sensors.

DETAILED DESCRIPTION

Each of the features and teachings disclosed herein can be utilized separately or in conjunction with other features and teachings to provide a hand prosthetic structure. Representative examples utilizing many of these additional features and teachings, both separately and in combination are described in further detail with reference to the attached figures. This detailed description is merely intended to teach a person of skill in the art further details for practicing the present teachings and is not intended to limit the scope of the claims. Therefore, combinations of features disclosed in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that each of these specific details are not required to practice the teachings of the present disclosure.

Moreover, the various features of the representative examples may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples. In this document, measurements, values, shapes, angles, and geometric references (such as perpendicularity and parallelism), when associated with words like "about" or other similar terms such as "approximately" or "substantially," should be construed to allow for measurement errors or others errors due to production and/or manufacture process, and may vary by up to ten percent.

Figure 1:
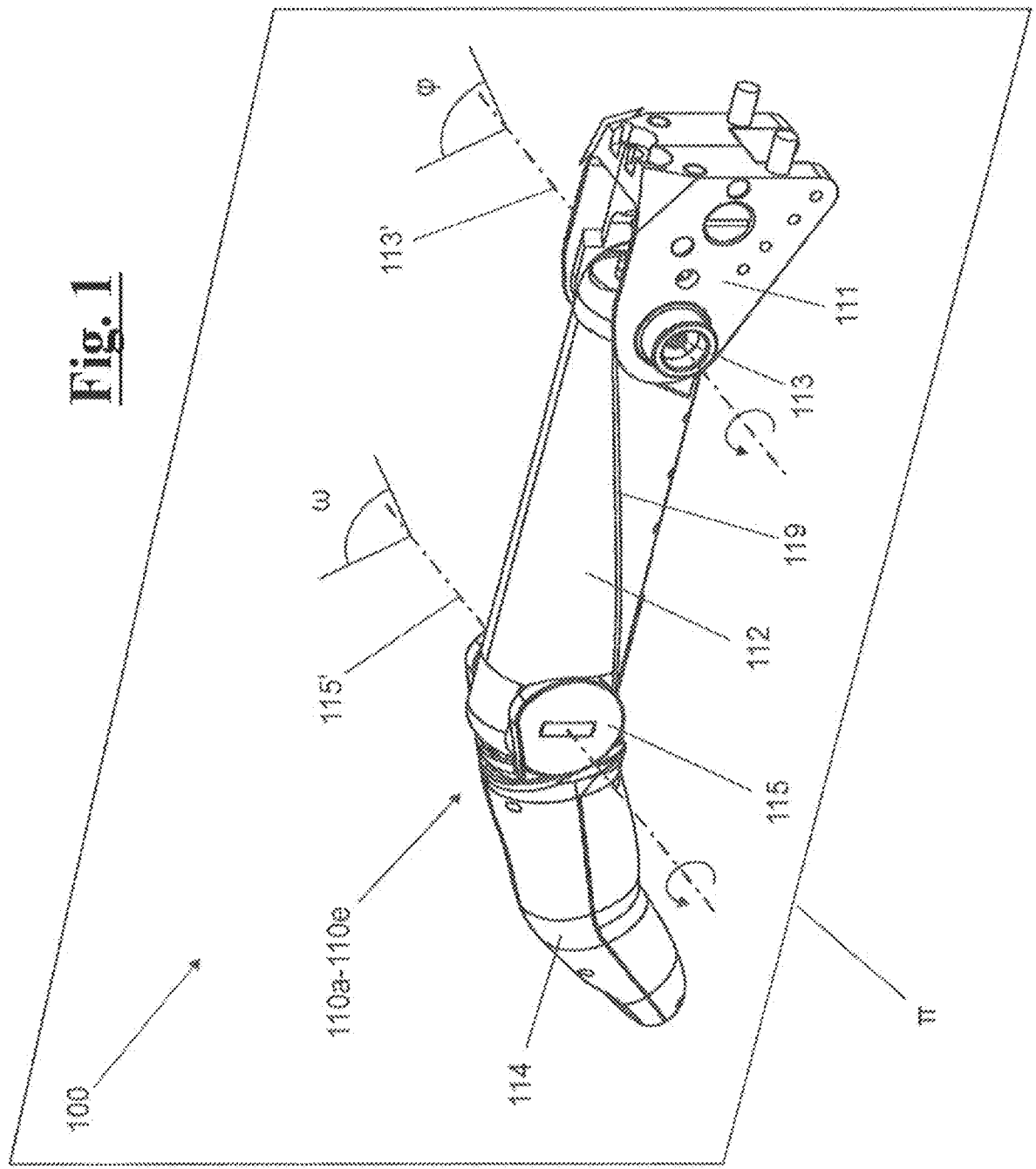
FIG. 1 shows a perspective view of an exemplary embodiment of the hand prosthetic structure, where a single mechanical finger is provided.

With reference to FIG. 1, an exemplary embodiment of the prosthetic hand structure 100 includes a mechanical finger 110a-110e. The mechanical finger has a metacarpal support 111, a proximal stiff link 112 and a distal stiff link 114. In this example, the proximal stiff link 112 can rotate an angle φ, about an axis 113', with respect to metacarpal support 111 by a proximal cylindrical joint 113. Similarly, distal stiff link 114 can rotate an angle ω, about an axis 115', with respect to proximal stiff link 112 a distal cylindrical joint 115. Both rotation axes 113' and 115' are substantially orthogonal to a plane π, in which angles φ and ω lay.

In this exemplary embodiment, the distal cylindrical joint 115 can be under-actuated by a belt 119 that is wound/unwound in guiding grooves or by a mechanical reduction gear made by a couple of gears (not shown in the figures). The choice of under-actuation allows a higher biomimetic of the prosthetic limb and assists a grip of objects, for example cylinders of small diameter, with a grip that otherwise would be achievable in a difficult way.

Alternatively, the distal cylindrical joint 115 can be missing, or be subject to a condition of stiff constraint, i.e. it is rigidly connected to the proximal stiff link, in such a way that the mechanical finger is substantially a mono-phalangeous finger. This may provide a reduction of costs of the product and an increase of performances versus force, since a certain amount of the energy available to the system is not consumed by under-actuating distal stiff link 114.

With reference to FIGS. 2 and 2A, in one embodiment, mechanical finger 110a-110e also includes a worm screw 116, arranged in proximal stiff link 112, a flexible rack 117 that meshes worm screw 116, and an actuator 118 arranged to cause the rotation of worm screw 116 about an axis 116'. In this example, flexible rack 117 includes a first end portion 117a, connected to metacarpal support 111, in order to rotate with respect to the latter, and a second end portion 117b that meshes the threaded profile of worm screw 116 at the gear P. This way, when the actuator 118 causes worm screw 116 to rotate, the second end portion 117b of flexible rack 117 translates along a direction substantially parallel to axis 116', distancing/approaching engagement zone P away from/towards first end 117a, with subsequent rotation, of a predetermined amplitude φ, of proximal stiff link 112 about its axis 113'.

In this embodiment, by approaching engagement zone P to first end 117a, a rotation suitable for bending mechanical finger 110a-110e corresponds. Vice-versa, by distancing engagement zone P to first end 117a corresponds to an extension of mechanical finger 110a-110e. The particular mechanical nature of flexible rack 117 allows it to work as pulling element, like a human tendon, when bending the mechanical finger 110a-110e, and also it works as pushing element during the extension. Furthermore, the high flexibility of rack 117 allows buckling, such that compressive loads are not transferred integrally to the stump, as it would occur in case of fingers stiff, but that receive a high damping, exactly as it happens with the fingers humane. By way of example only, and not by way of limitation, the rack can be made of super-elastic material, in order to meet as far as possible the flexibility requirement.

Figure 3A:
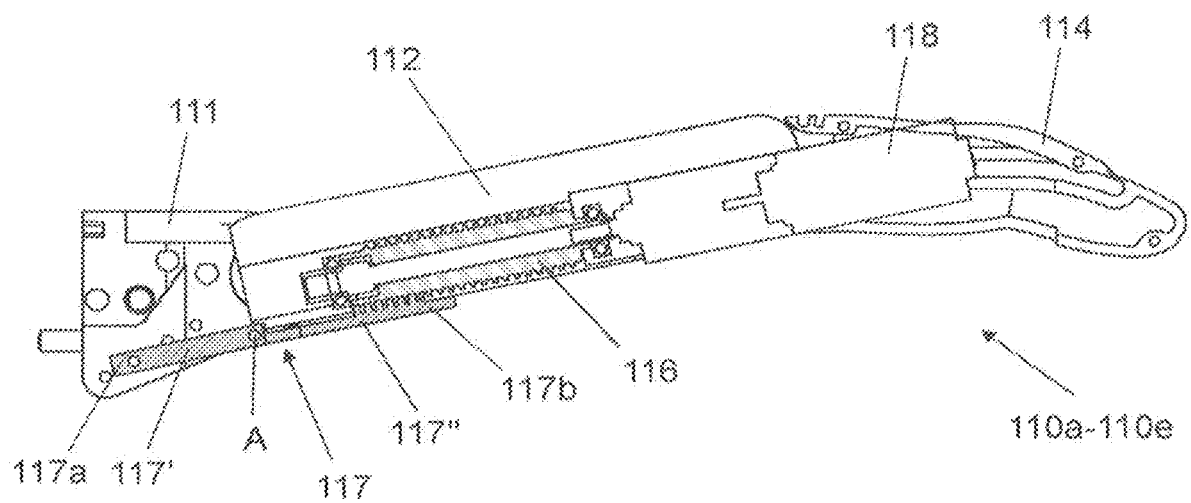
FIGS. 3A and 3B show a cross section, respectively in an extension and bending movement, of an alternative exemplary embodiment of the hand prosthetic structure, where the rack is made of two segments, a stiff segment and a flexible segment.
Figure 3B:
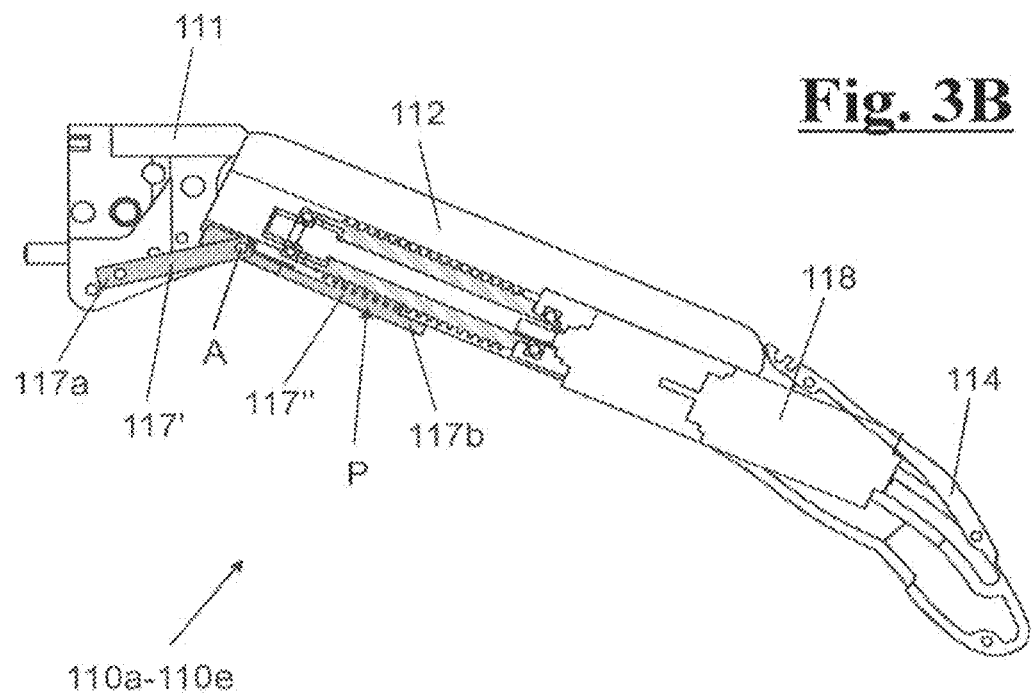

In FIGS. 3A and 3B an exemplary alternative embodiment is shown of mechanical finger 110a-110e, where flexible rack 117 is made of two segments 117', 117" pivotally connected by pivot A. In this embodiment, segment 117', including first end 117a, is made of a material having a predetermined flexibility. It can correspond to the predetermined flexibility for flexible rack 117, or it can be lower than it. In the latter case, the predetermined flexibility of segment 117' may be obtained by introducing at least one spring. In this example, segment 117" including second end 117b is made of stiff material, so that it can mesh better, at zone P, with worm screw 116. The operation of rack 117, in this alternative exemplary embodiment is similar to that of rack 117 of FIG. 2.

Figure 5:
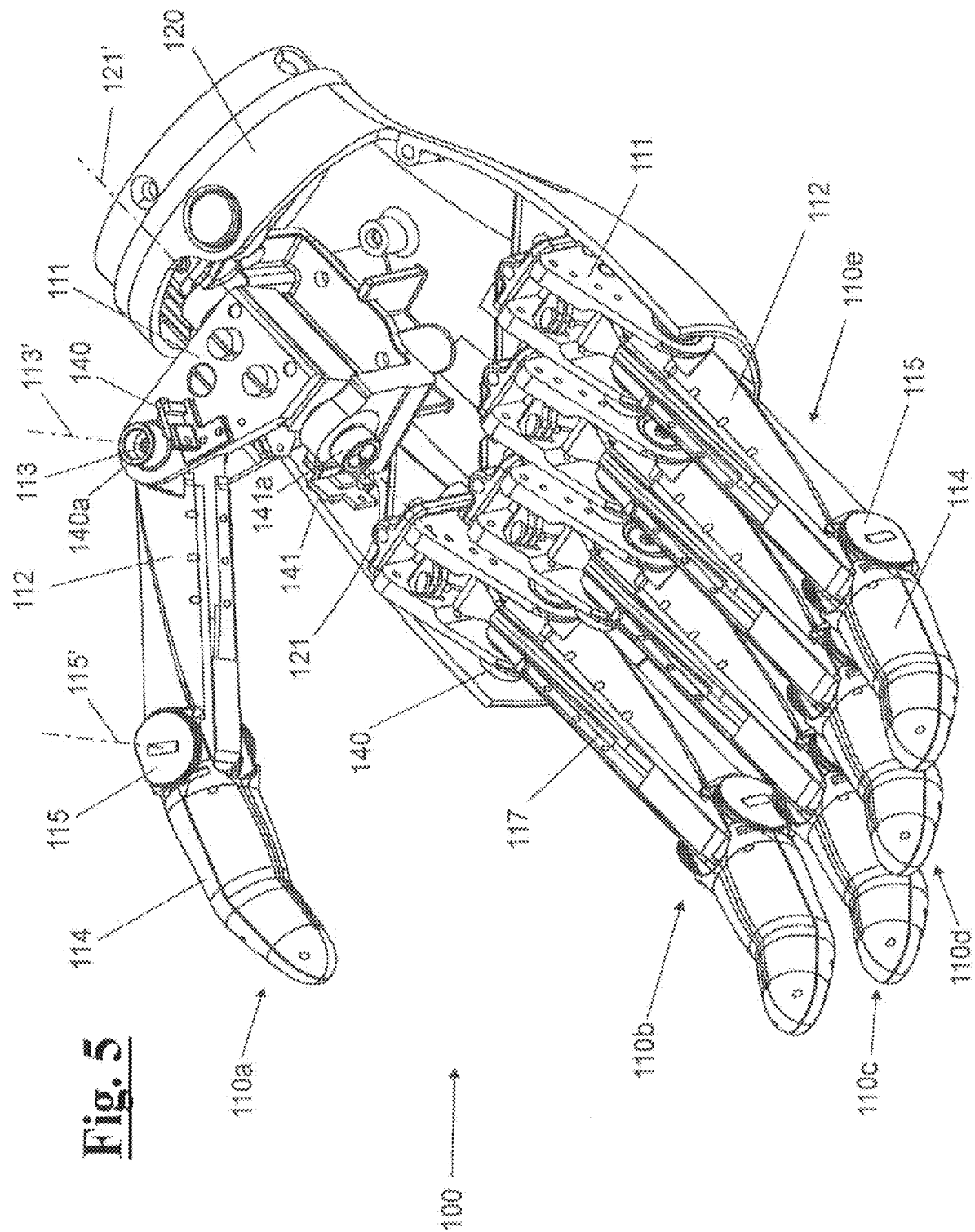
FIG. 5 shows the same exemplary embodiment of FIG. 4, where the palm cover of the metacarpal base is removed for depicting the cylinder-piston mechanism.

With reference to FIGS. 4 and 5, an exemplary embodiment of the prosthetic hand structure 100 includes five mechanical fingers 110a-110e, which can be in the form shown in FIG. 1, and a metacarpal base 120 connected to metacarpal supports 111 of mechanical fingers 110a-110e. As shown, metacarpal base 120, further to connecting mechanical fingers 110a-110e with each other, provides also higher biomimetic features to the whole prosthetic structure. The mechanical finger used as index finger 110b, the mechanical finger used as middle finger 110c, the mechanical finger used as ring finger 110d and the mechanical finger used as little finger 110*e* can be arranged in such a way that the planes 7C of each mechanical finger 110*b*-110*e* are parallel to each other. The mechanical finger used as thumb 110*a* lays in a plane not parallel to the planes π.

However, in exemplary embodiments not shown in the figure, for mechanical fingers 110*b*-110*e* that correspond to the index, middle, ring and little fingers, the planes π can be incident to each other to generate the adduction/abduction movement of the fingers.

In one example, with reference to FIG. 5, metacarpal support 111 of the mechanical finger used as thumb 110*a* is connected to the metacarpal base 120 by a rotational joint 121 that allows mechanical finger 110*a* rotating about an axis 121' substantially orthogonal to rotation axes 113' and 115'. This way, the mechanical finger for the thumb 110*a* is equipped with the abduction/adduction degree of freedom, essential for broadening the range of the possible grips that can be made with the above described prosthetic structure 100. Rotational joint 121 can be passive, as in the case of the figures, or actuated. In the case of a passive joint, the user can position the other hand with the thumb in a predetermined working configuration, selected from a variety of possible gripping configurations.

Figure 6:
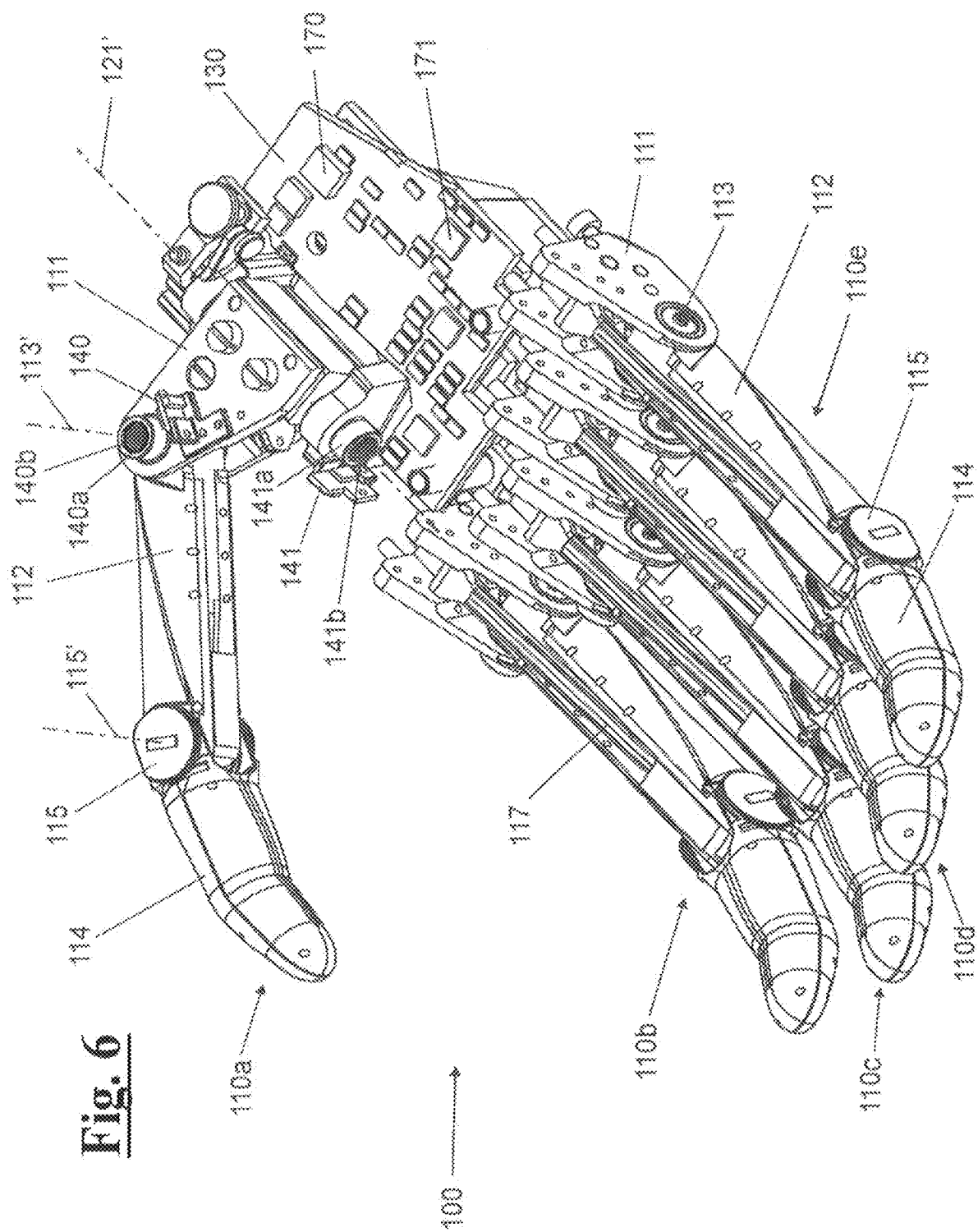
FIG. 6 shows the same exemplary embodiment of FIG. 4, where the metacarpal base is omitted and the control unit is shown.

In FIG. 5 the feedback position sensor 140 of the thumb is also shown, and may be configured to measure the position of proximal stiff link 112 of mechanical finger 110*a* with respect to metacarpal support 111. The feedback position sensor 140 may then determine in real time the amplitude $\varphi$ of the rotation of proximal stiff link 112 about its axis 113', in order to generate instantly a corresponding feedback signal and to transmit this feedback signal to a control unit 130 (as shown in FIG. 6). In one example, the feedback position sensor 140 of the thumb may need, for a correct operation, to measure magnetic field changes. To this purpose, at joint 113 a housing 140*a* is arranged in which a magnet is inserted 140*b* (FIG. 6). Such magnet is integral to proximal stiff link 112 of mechanical finger 110*a* and allows Hall-effect sensor 140 detecting the rotation about its axis 113', allowing the generation of the feedback signal. Control unit 130 computes then the feedback signal and operates the actuator 118 for actuating worm screw 116, until the amplitude $\varphi$ determined in real time fits predetermined amplitude $\varphi$.

Figure 7:
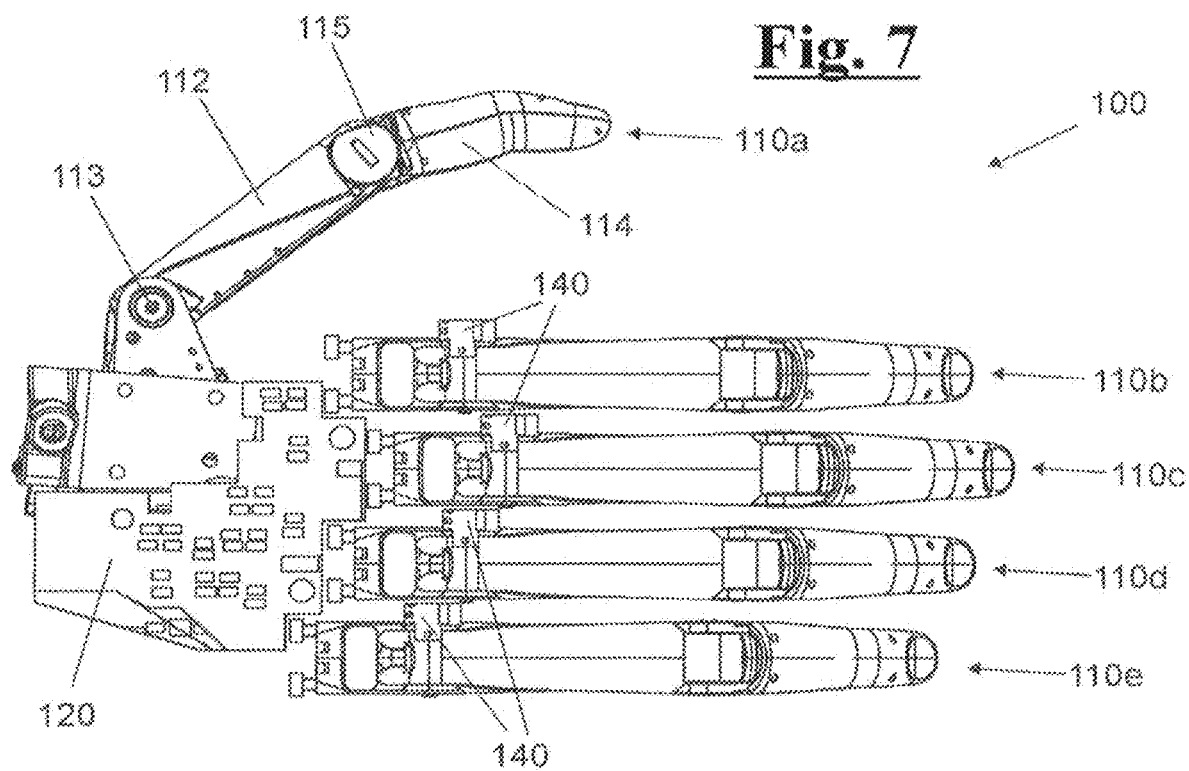
FIGS. 7 and 8 show in a view, respectively, from the above and lateral, the exemplary embodiment of FIG. 6.
Figure 8:
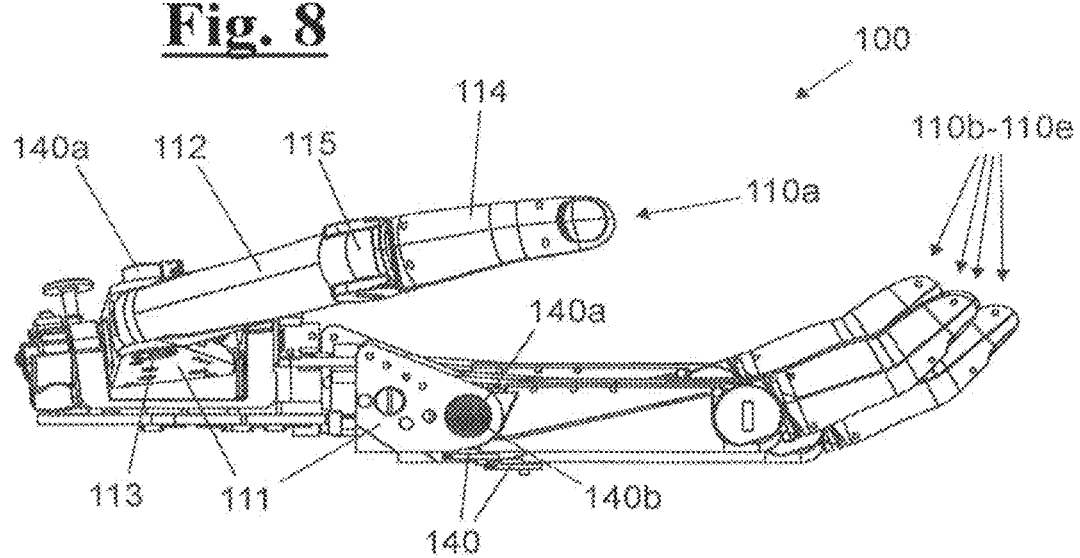

In FIGS. 6, 7 and 8 the same exemplary embodiment of prosthetic structure 100 of FIGS. 4 and 5 is shown, where however, for simplicity, the control unit 130 is shown and metacarpal base 120 is hidden. In FIGS. 7 and 8 the feedback sensors 140 relative to mechanical fingers 110*b*-110*e* is shown. Furthermore, in FIG. 8, the housing 140*a* and the magnet 140*b* relative to feedback sensor 140 of mechanical finger 110*b* are shown.

Figure 9:
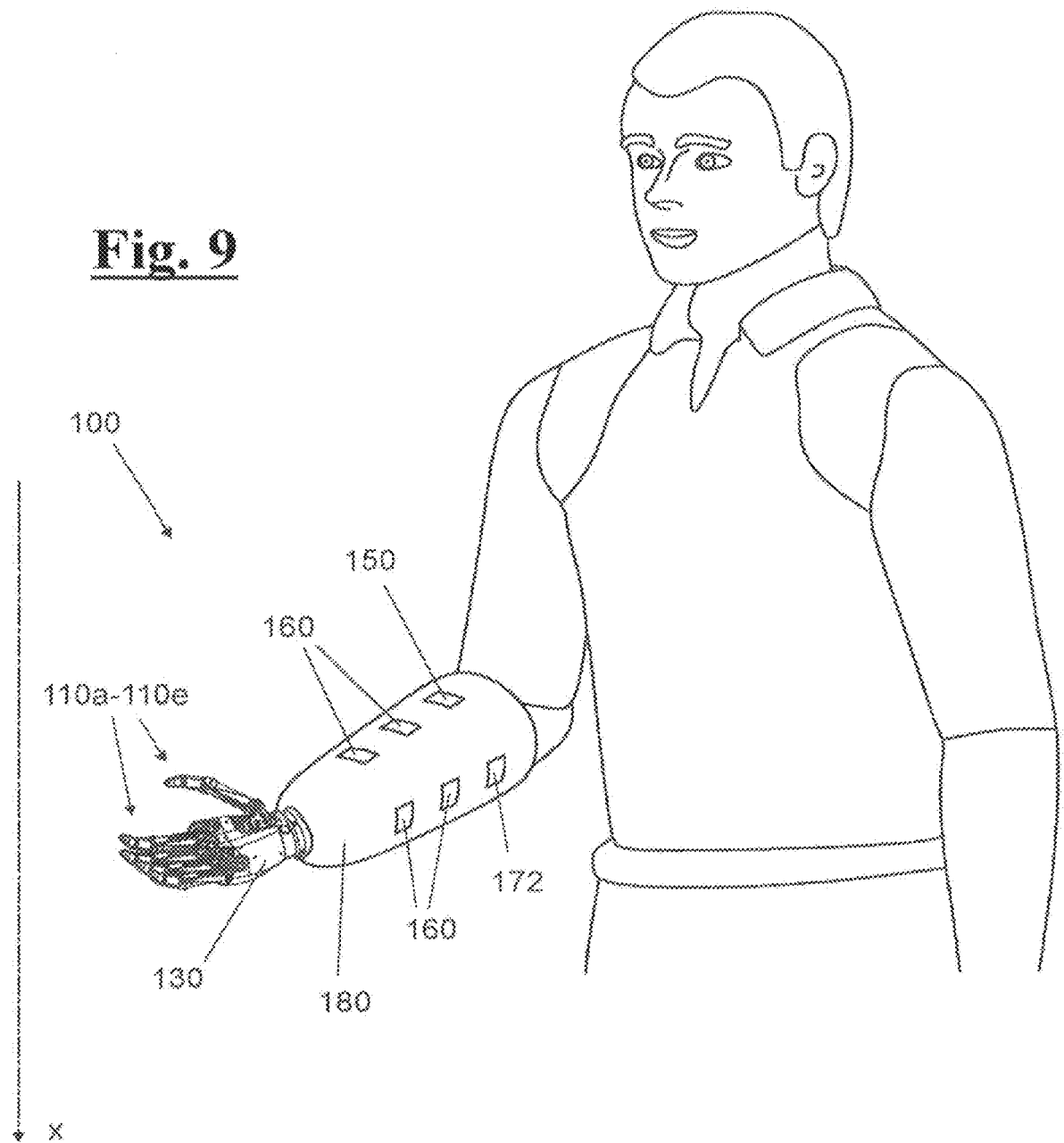
FIG. 9 shows an exemplary embodiment of a hand prosthetic structure, applied to a patient, and including a support body for sensors in the structure.

FIG. 9 shows one embodiment of the prosthesis structure 100 including a support body, or cup 180. The support body or cup 180 has a substantially cylindrical or frustoconical shape in this embodiment, which is put on the stump of the patient and arranged to support part of the sensor types necessary to detect the intentions of the patient, and to transmit it to control unit 130, in order to carry out correctly mechanical fingers 110*a*-110*e*.

In the exemplary embodiment of FIG. 9, the following elements can be arranged on the support body 180:
  a myoelectric sensor 150 configured to measure a voltage associated with the activation of an agonist and/or antagonist muscle of the stump of the patient and to generate a relative myoelectric signal; and
  a plurality of force sensors 160 configured to measure a plurality of pressure data corresponding to a predetermined muscle configuration achieved by the patient and to generate at least one corresponding signal responsive to the distribution of pressure on the stump.

The myoelectric signal and the pressure distribution signal are then computed by control unit 130, in such a way that control unit 130 selects a predetermined working configuration. Such working configuration, in particular a gripping configuration, corresponds to one among a plurality of predetermined configurations, better interpreting the will of the patient. Control unit 130 operates then the actuators 118 in such a way that mechanical fingers 110*a*-110*e* perform the selected configuration.

In addition to the above described sensors, prosthetic structure 100 may also include other sensors that allow a quicker and more precise selection of the predetermined configuration chosen by the patient and/or that allow having a high number of predetermined configurations among which to carry out the selection. For example, such sensors can be:
  an inertial sensor 170, which is located for example on the metacarpal base 120 or in control unit 130 (FIG. 6), configured to measure the spatial orientation of prosthetic structure 100 with respect to a predetermined direction x, to generate a corresponding spatial position signal, and to transmit this spatial position signal to control unit 130;
  an inertial sensor 171, which is located for example on the metacarpal base 120 or in control unit 130 (FIG. 6), configured to measure at least one linear and/or angular speed and/or acceleration, of metacarpal base 120, to generate a corresponding kinematic signal, and to transmit this kinematic signal to the control unit (130);
  an inertial sensor 172, which is located for example on cup 180 and coupled to sensor 171, configured to measure at least one linear and/or angular speed and/or acceleration, of the forearm, to generate a corresponding reference spatial position signal, and to transmit this reference spatial position signal to the control unit (130), in order to calculate the relative position between hand and forearm and therefore the rate of inclination of the wrist; and
  a position sensor for the thumb 141 (FIG. 5), in particular a Hall-effect sensor, configured to measure the direction of the mechanical finger for the thumb 110*a* with respect to the metacarpal base 120, in particular the angle of abduction/adduction, to generate a corresponding thumb position signal, and to transmit this thumb position signal to control unit 130.

In one embodiment, the position sensor for the thumb 141 operates too with feedback sensors 140 above described. As shown in FIG. 6, in fact, at joint 121 a housing 141*a* is arranged in which a magnet 141*b* is inserted. Such magnet is integral to metacarpal support 111 of mechanical finger 110*a* and allows Hall-effect sensor 141 detecting the rotation about its axis 121', and then generating the thumb position signal. The sensors above described can be used in combination or as an alternative to each other.

Figure 10:
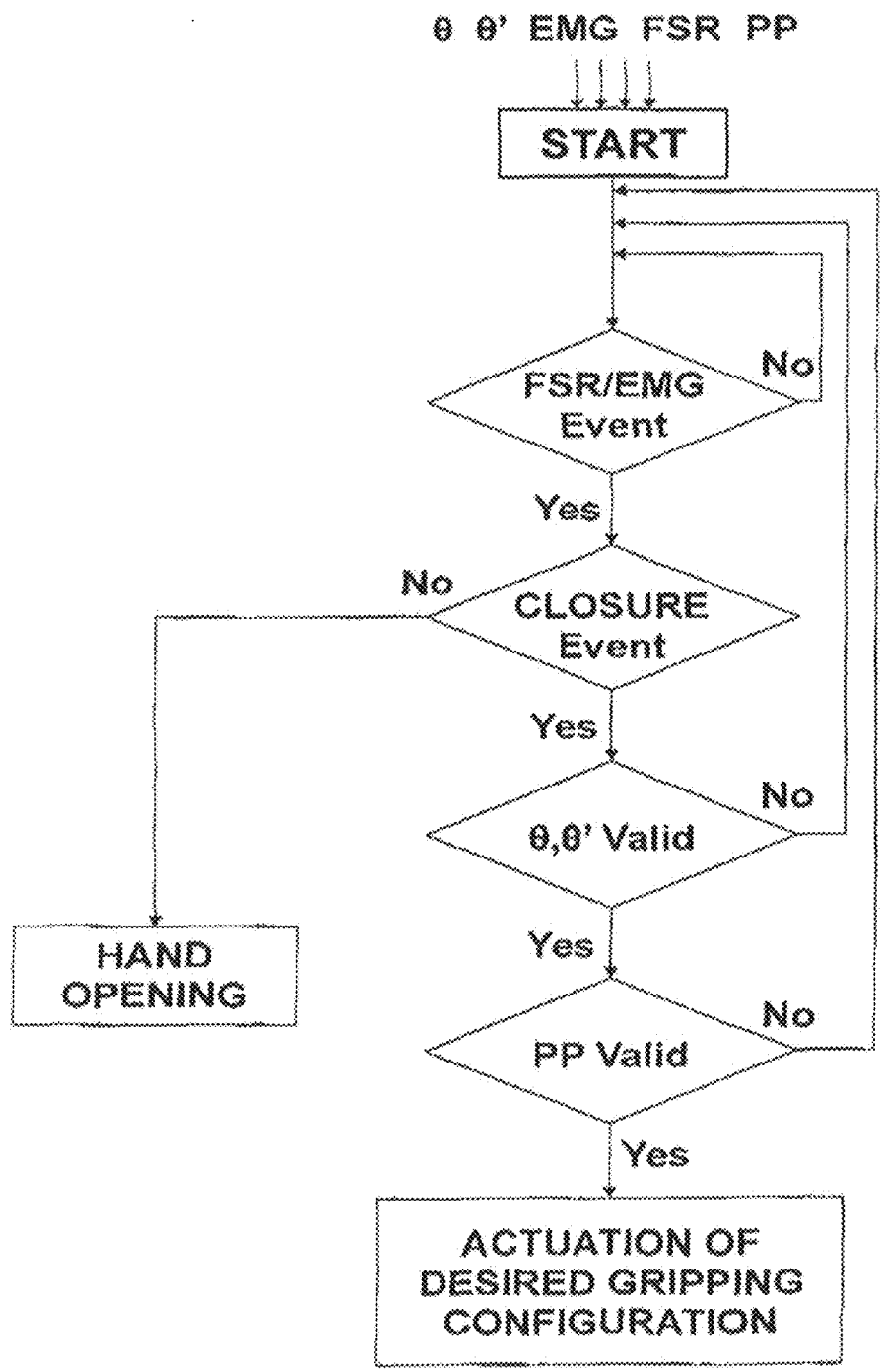
FIG. 10 shows a possible diagrammatical view of the operation of an algorithm configured to analyze the signals detected by different sensors.

In the block diagram of FIG. 10, an example is diagrammatically shown of a possible algorithm that can be associated with control unit 130 for analyzing the signals detected by the different sensors. The signals considered by the algorithm in this example are the myoelectric signal (EMG), the pressure distribution signal (FSR), the spatial position signal ($\theta$), as well as the kinematic signal ($\theta'$) and the thumb position signal (PP). For simplicity, the shown algorithm takes into account only a possible open configuration of the hand.

In this embodiment, the algorithm defines a priority sorting of the main input signals, in order to discriminate at each passage any gripping configurations incompatible with the received signals and determine univocally the gripping configuration desired by the patient. In particular, when control unit 130 receives a signal EMG and/or a signal FSR (event FSR/EMG), it discriminates, according to this signal, if the patient has given a closure command (positive closure event) or an opening command (negative closure event). If the patient has given an opening command, control unit 130 operates actuators 118 in order to bring mechanical fingers 110*a*-110*e* to the open configuration of the hand. This is because, as starting hypothesis, there is only one open configuration, and therefore the configuration is univocally predetermined without further controls on the signals.

If the patient has given a closing command, it is possible that control unit 130 has already enough data from the EMG and FSR signals for excluding some gripping configurations that are not compatible with such signals. Then, the algorithm proceeds with the following analysis of the signals. The signals $\theta$ and $\theta'$ are then analyzed, relative to the position, the speed and the accelerations of the prosthetic structure. If such signals are compatible with at least one gripping configuration among those that are not excluded in the preliminary step (positive validation of $\theta$ and $\theta'$), then the algorithm proceeds with the successive step, excluding possible gripping configurations that are not compatible with the values of the signals $\theta$ and $\theta'$ detected by control unit 130.

Alternatively, in case of negative validation of the signals $\theta$ and $\theta'$, i.e. in case no gripping configurations are found compatible with the values of the signals $\theta$ and $\theta'$ detected by control unit 130, the algorithm returns to the starting step and control unit 130 does not give any actuation command. Similar situations occur in the successive step, concerning the validation of the thumb position signal PP. The principles of the algorithm can be then extended at any signal that the control unit can receive, in order to select gradually the range of possible gripping configurations.

After having validated all signals, the algorithm can identify in an univocal way the gripping configuration desired by the patient. In any case, to avoid errors to the prosthesis, a final step of the algorithm (not shown in FIG. 10) can be provided that operates the actuation only when a gripping configuration has been univocally predetermined. If more than one gripping configuration has been found compatible, then the algorithm returns to the starting step, and control unit 130 does not give any actuation command.

In FIG. 11, an example is shown of a 3D vector space generated by the signals transmitted from the sensors to control unit 130. In this example, the signals transmitted from the sensors to control unit 130 generates a vector space with N dimensions, where each Nth dimension corresponds to a parameter detected by the sensors or to a quantity deriving from this parameter. In this vector space a plurality of subspaces is detected, each of which corresponds to a particular gripping configuration. In particular, each gripping configuration is defined by a combination of N coordinates, each Nth coordinate corresponding to a range of values of the parameter corresponding to the Nth dimensions vector.

In the example of FIG. 11, the vector space is generated using 3 parameters and defines then a volumetric space. In this space, two volumes A and B are shown, corresponding to two particular gripping configurations and defined by a combination of three ranges of values. In this case, the algorithm of FIG. 10 may carry out 3 steps of validation, one for each parameter. In a first step the algorithm is configured to exclude all the gripping configurations whose range of values of the first parameter does not include the value of the parameter detected by the sensor. In a second step the algorithm is configured to test the compatibility of the value of the second parameter detected with the residue gripping configurations deriving from the previous step. If this value is in the range of values of the second parameter of at least one of such residue gripping configurations, then the algorithm passes through the third step, where the same procedure is repeated. If the vector subspaces defining the different gripping configurations do not have intersections with each other, then certainly each combination of values of the parameters defines univocally a gripping configuration, and the control unit can give the actuation command.

Figure 12A:
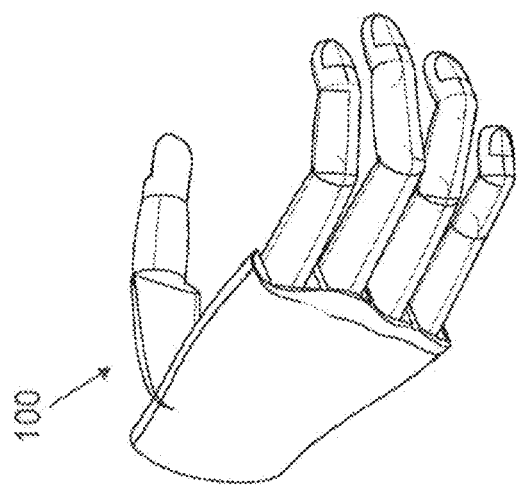
FIGS. 12a-12f show some of the possible working configurations obtainable from the above described prosthetic structure.
Figure 12C:
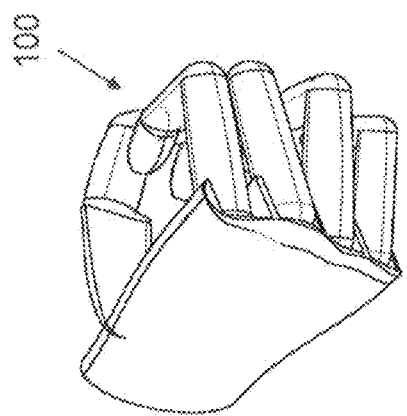
Figure 12B:
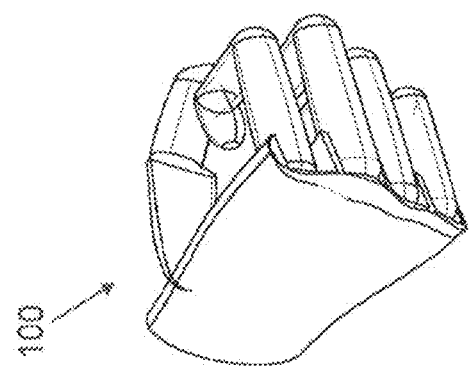
Figure 12E:
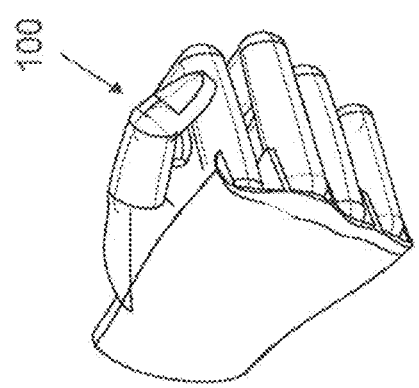
Figure 12D:
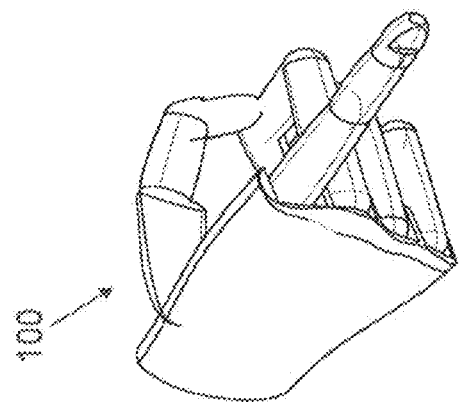
Figure 12F:
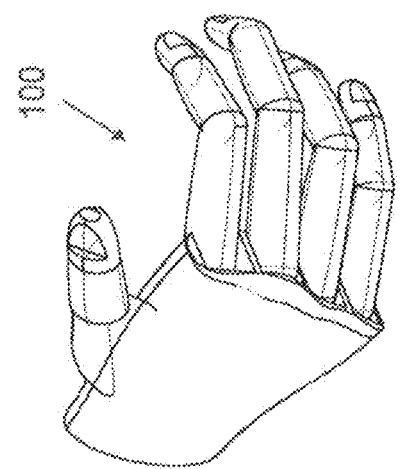

Graphically, the lines 20 define the trajectories obtained from the subsets of three parameters during the use of the prosthesis. When a trajectory crosses a volume associated with a gripping configuration, the prosthesis performs such gripping configuration. In FIGS. 12A to 12E some of the possible gripping configurations are shown obtainable from the above described prosthetic structure. In these examples, FIG. 12A shows a grip with the index finger, FIG. 12B shows a hook-like grip, FIG. 12C shows a cylindrical palm grip with thumb in opposition, FIG. 12D shows a cylindrical palm grip on objects of big diameter, FIG. 12F shows a key grip, and FIG. 12E shows a grip on cylinders of small size.

One of ordinary skill in the art will appreciate that not all hand prosthetic structures have all these components and may have other components in addition to, or in lieu of, those components mentioned here. Furthermore, while these components are viewed and described separately, various components may be integrated into a single unit in some embodiments.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A prosthetic hand structure, comprising:
   at least one mechanical finger having a metacarpal support, a proximal stiff link connected to the metacarpal support by a proximal cylindrical joint, the proximal stiff link arranged for carrying out a rotation of the proximal stiff link of a first predetermined amplitude with respect to the metacarpal support about an axis of the proximal cylindrical joint, said at least one mechanical finger including a distal stiff link connected to the proximal stiff link by a distal cylindrical joint, the distal stiff link being arranged for carrying out a rotation of the distal stiff link of a second predetermined amplitude with respect to the proximal stiff link about an axis of the distal cylindrical joint;
   a transmission member connected to the proximal stiff link, the transmission member arranged to actuate the proximal stiff link in order to cause the rotation of the proximal stiff link of the first predetermined amplitude, the transmission member comprising a worm screw having a threaded profile, the worm screw being integral with the proximal stiff link and arranged for carrying out a rotation of the worm screw about a longitudinal axis of the worm screw, the transmission member further comprising a flexible rack having a first end portion pivotally connected to the metacarpal support and a second end portion arranged to engage with a thread of the worm screw at an engagement zone of the flexible rack, wherein the flexible rack is configured to buckle such that compressive loads are not transferred integrally to the metacarpal support, and wherein the second end portion of the flexible rack is configured to translate along a direction substantially parallel to an axis of the worm screw, as the transmission member actuates the proximal stiff link, wherein in distancing the engagement zone away from the first end portion, the second end portion extends into the distal stiff link;

an actuator mounted to said at least one mechanical finger, the actuator arranged to actuate the worm screw of the transmission member to obtain the rotation of the worm screw about the longitudinal axis of the worm screw, in such a way that, when the actuator actuates the worm screw, there is a moving-away movement of the engagement zone from the first end portion, se wherein the second end portion of the flexible rack extends into the distal stiff link, or an approaching movement of the engagement zone to the first end portion, causing the rotation of the proximal stiff link of the first predetermined amplitude, in a direction of rotation, or in an opposite direction of rotation, of the proximal stiff link about the axis of the proximal cylindrical joint, the rotation of the proximal stiff link of the first predetermined amplitude corresponding to an extension or flexion movement of said at least one mechanical finger;

at least one feedback position sensor associated with said at least one mechanical finger, said at least one feedback position sensor being configured to measure a position of the proximal stiff link with respect to the metacarpal support for determining in real time an amplitude of rotation of the proximal stiff link, the feedback position sensor being configured to generate a corresponding feedback signal; and a control unit connected to the feedback position sensor to receive the feedback signal, the control unit being configured to analyze the feedback signal and to operate the actuator to actuate the worm screw until the amplitude determined in real time meets the first predetermined amplitude.

2. The prosthetic hand structure of claim 1, wherein the rotation of the proximal stiff link of the first predetermined amplitude lies in a plane substantially orthogonal to the axis of the proximal cylindrical joint.

3. The prosthetic hand structure of claim 2, wherein the worm screw is adapted to carry out a rotation about a rotation axis of the worm screw, the rotation axis of the worm screw arranged in the plane substantially orthogonal to the axis of the proximal cylindrical joint.

4. The prosthetic hand structure of claim 1, wherein said at least one mechanical finger includes a distal stiff link connected to the proximal stiff link by a distal cylindrical joint, the distal stiff link being arranged for carrying out a rotation of the distal stiff link of the second predetermined amplitude with respect to the proximal stiff link about an axis of the distal cylindrical joint.

5. The prosthetic hand structure of claim 4, wherein the distal cylindrical joint is under-actuated by mechanical reduction gears or a belt.

6. The prosthetic hand structure of claim 1, wherein said at least one mechanical figure comprises a plurality of mechanical fingers including a mechanical finger for use as a thumb, the prosthetic hand structure further comprising: a metacarpal base, the metacarpal support of each mechanical finger of the plurality of the plurality of mechanical figures being connected to the metacarpal base, wherein the mechanical finger for use as the thumb is connected to the metacarpal base by a rotational joint to provide to the mechanical finger for use as the thumb an abduction or adduction degree of freedom.

7. The prosthetic hand structure of claim 1, wherein the feedback position sensor is a Hall-effect sensor.

8. The prosthetic hand structure of claim 1, further comprising at least one myoelectric sensor arranged, in use, in contact with a stump of a patient, the myoelectric sensor configured to measure a voltage associated with activation of an agonist or antagonist muscle of the stump of the patient and to generate a myoelectric signal.

9. The prosthetic hand structure of claim 8, further comprising a plurality of force sensors arranged, in use, in contact with the stump of the patient and distributed on a predetermined surface of the stump, the plurality of force sensors configured to measure a plurality of pressure data corresponding to a predetermined muscle configuration achieved by the patient and to generate at least one pressure distribution signal indicative of the plurality of pressure data measured on the stump.

10. The prosthetic hand structure of claim 9, wherein the control unit is configured to analyze the myoelectric signal and the pressure distribution signal and to carry out a selection of a predetermined working configuration among a plurality of possible predetermined working configurations, the control unit arranged to operate the actuator, to obtain the selected working configuration.

11. The prosthetic hand structure of claim 10, wherein the control unit performs the selection among the plurality of possible predetermined working configurations comparing the myoelectric signal and the pressure distribution signal predetermined by the myoelectric sensor and the plurality of force sensors with a plurality of signals associated with predetermined working configurations.

12. The prosthetic hand structure of claim 11, further comprising at least one inertial sensor selected from the group consisting of:

an inertial sensor configured to measure a spatial orientation of the prosthetic hand structure with respect to a predetermined direction, to generate a corresponding spatial position signal, and to transmit the spatial position signal to the control unit; and an inertial sensor configured to measure at least one linear speed, angular speed, or acceleration of the prosthetic hand structure, to generate a corresponding kinematic signal, and to transmit the kinematic signal to the control unit.

13. The prosthetic hand structure, of claim 12, wherein the control unit is arranged to carry out the selection of possible working configurations also on the basis of the spatial position signal or the kinematic signal.

* * * * *